US010213188B2

(12) United States Patent
Song et al.

(10) Patent No.: US 10,213,188 B2
(45) Date of Patent: Feb. 26, 2019

(54) HIGH VOLTAGE SWITCHING CIRCUIT AND ULTRASOUND PROBE

(71) Applicants: SAMSUNG ELECTRONICS CO., LTD., Suwon-si (KR); Industry-University Cooperation Foundation Hanyang University, Seoul (KR)

(72) Inventors: Jong Keun Song, Yongin-si (KR); Taeho Jeon, Seoul (KR); Oh-Kyong Kwon, Seoul (KR); Sung-Jin Jung, Seoul (KR)

(73) Assignees: SAMSUNG ELECTRONICS CO., LTD., Suwon-si (KR); Industry-University Cooperation Foundation Hanyang University, Seoul (KR)

( * ) Notice: Subject to any disclaimer, the term of this patent is extended or adjusted under 35 U.S.C. 154(b) by 774 days.

(21) Appl. No.: 14/715,907

(22) Filed: May 19, 2015

(65) Prior Publication Data

US 2015/0333627 A1 Nov. 19, 2015

(30) Foreign Application Priority Data

May 19, 2014 (KR) ........................ 10-2014-0059862

(51) Int. Cl.
*A61B 8/00* (2006.01)
*A61B 8/14* (2006.01)
*H02M 3/158* (2006.01)
*H03K 17/10* (2006.01)
*H03K 17/687* (2006.01)
*G01S 7/52* (2006.01)

(52) U.S. Cl.
CPC ............ *A61B 8/56* (2013.01); *A61B 8/14* (2013.01); *H02M 3/158* (2013.01); *H03K 17/102* (2013.01); *H03K 17/6874* (2013.01); *G01S 7/52017* (2013.01); *H03K 2217/0081* (2013.01); *Y10T 307/549* (2015.04)

(58) Field of Classification Search
CPC ............ A61B 8/14; A61B 8/56; H02M 3/158; H03K 17/102; H03K 17/6874; H03K 2217/0081; Y10T 307/549; G01S 7/52017
See application file for complete search history.

(56) References Cited

U.S. PATENT DOCUMENTS

2001/0043090 A1* 11/2001 Savord ............... B06B 1/0207
327/108
2005/0154300 A1* 7/2005 Wodnicki ........... B06B 1/0215
600/437

* cited by examiner

*Primary Examiner* — Bo Joseph Peng
(74) *Attorney, Agent, or Firm* — Sughrue Mion, PLLC

(57) ABSTRACT

Disclosed herein are a high voltage switching circuit which includes one or more main switching devices connected to one or more current sources, and a control circuit unit configured to control a potential difference between terminals of each of the main switching devices within a predetermined range by receiving current from the one or more current sources.

8 Claims, 9 Drawing Sheets

HIGH VOLTAGE SWITCHING CIRCUIT AND ULTRASOUND PROBE

CROSS-REFERENCE TO RELATED APPLICATION(S)

This application claims priority from Korean Patent Application No. 10-2014-0059862, filed on May 19, 2014 in the Korean Intellectual Property Office, the disclosure of which is incorporated herein by reference in its entirety.

BACKGROUND

1. Field

Exemplary embodiments relate to high voltage switching circuits and ultrasound probes.

2. Description of the Related Art

A high voltage switching circuit prevents a circuit from being damaged by blocking a high-voltage-level signal.

In apparatuses which include a semiconductor switch device, a capacitor, an inductor, and the like, when an input voltage exceeds a maximum allowable input voltage of each device, voltage stress of each device increases, thereby causing a breakdown of each device. Thus, a semiconductor integrated circuit in which various voltages are used requires a high voltage switching circuit in order to prevent a high voltage signal output from a circuit which includes high voltage devices from being applied to a circuit which includes low voltage devices, and to transmit and receive a low voltage output signal of a circuit which includes the low voltage devices.

For example, circuits which are configured for transmitting and receiving ultrasonic waves in a two-dimensional or three-dimensional ultrasonic diagnosis apparatus are integrated under an ultrasound transducer or connected to the ultrasound transducer via a cable. Here, since a low voltage-receiving circuit needs to be protected from a high voltage signal applied to the transducer from a high voltage-transmitting circuit, and a signal output from the transducer needs to be transferred to the low voltage-receiving circuit, a high voltage switching circuit is required.

SUMMARY

Therefore, it is an aspect of one or more exemplary embodiments to provide a high voltage switching circuit which controls a potential difference between terminals, and an ultrasound probe.

Additional aspects of the exemplary embodiments will be set forth in part in the description which follows and, in part, will be obvious from the description, or may be learned by practice of the exemplary embodiments.

In accordance with one aspect of one or more exemplary embodiments, a high voltage switching circuit includes at least one main switching device connected to at least one current source and a control circuit configured to control a potential difference between respective terminals of each of the at least one main switching device by receiving current from the at least one current source such that the potential difference is within a predetermined range.

The control circuit may include two low voltage switching devices and one high voltage switching device.

A first main switching device from among the at least one main switching device may be connected to a first current source from among the at least one current source and a first input/output terminal of the high voltage switching circuit, and a second main switching device from among the at least one main switching device may be connected to the first current source and a second input/output terminal of the high voltage switching circuit.

A first low voltage switching device from among the two low voltage switching devices may be controlled by a first current source from among the at least one current source, and a second low voltage switching device from among the two low voltage switching devices may be controlled by a second current source from among the at least one current source.

A first low voltage switching device from among the two low voltage switching devices may include a p-type metal-oxide-semiconductor (PMOS) transistor, and each of a second low voltage switching device from among the two low voltage switching devices, the high voltage switching device, a first main switching device from among the at least one main switching device, and a second main switching device from among the at least one main switching device may include an n-type metal-oxide-semiconductor (NMOS) transistor.

The potential difference between the respective terminals of the at least one main switching device may include a potential difference between a respective gate terminal and a respective source terminal of the at least one main switching device, and a first current source from among the at least one current source may be configured to charge or discharge the respective gate terminal of the at least one main switching device and to control the control circuit, and a second current source from among the at least one current source may be configured to control the control circuit.

The high voltage switching circuit may further include a control signal generating circuit configured to control the at least one current source.

The control signal generating circuit unit may further include at least one level shifter.

Each of the at least one level shifter may include at least one high voltage switching device and an inverter.

In accordance with another aspect of one or more exemplary embodiments, an ultrasound probe includes a transducer, and a high voltage switching circuit configured to control a signal received by the transducer by blocking a signal which has a potential that is greater than a reference potential, in which the high voltage switching circuit includes at least one main switching device connected to at least one current source, and a control circuit configured to control a potential difference between respective terminals of each of the at least one main switching device by receiving current from the at least one current source such that the potential difference is within a predetermined range.

The control circuit may include two low voltage switching devices and one high voltage switching device.

A first main switching device from among the at least one main switching device may be connected to a first current source from among the at least one current source and a first input/output terminal of the high voltage switching circuit, and a second main switching device from among the at least one main switching device may be connected to the first current source and a second input/output terminal of the high voltage switching circuit.

A first low voltage switching device from among the two low voltage switching devices may be controlled by a first current source from among the at least one current source, and a second low voltage switching device from among the two low voltage switching devices may be controlled by a second current source from among the at least one current source.

A first low voltage switching device from among the two low voltage switching devices may include a p-type metal-oxide-semiconductor (PMOS) transistor, and each of a second low voltage switching device from among the two low voltage switching devices, the high voltage switching device, a first main switching device from among the at least one main switching device, and a second main switching device from among the at least one main switching device may include an n-type metal-oxide-semiconductor (NMOS) transistor.

The potential difference between the respective terminals of the at least one main switching device may include a potential difference between a respective gate terminal and a respective source terminal of the at least one main switching device, and a first current source from among the at least one current source may be configured to charge or discharge the respective gate terminal of the at least one main switching device and to control the control circuit, and a second current source from among the at least one current source may be configured to control the control circuit.

The high voltage switching circuit may further include a control signal generating circuit configured to control the at least one current source.

The control signal generating circuit unit may include at least one level shifter.

Each of the at least one level shifter may include at least one high voltage switching device and an inverter.

BRIEF DESCRIPTION OF THE DRAWINGS

These and/or other aspects will become apparent and more readily appreciated from the following description of exemplary embodiments, taken in conjunction with the accompanying drawings of which:

FIG. 7 is a flowchart illustrating a method for controlling a high voltage switching circuit when main switching devices in a turn-off state are turned on;

DETAILED DESCRIPTION

Reference will now be made in detail to exemplary embodiments, examples of which are illustrated in the accompanying drawings, wherein like reference numerals refer to like elements throughout. In the description of the exemplary embodiments, certain detailed explanations of related art are omitted when it is deemed that they may unnecessarily obscure the essence of the exemplary embodiments. It will be understood that although the terms "first", "second", etc. may be used herein to describe various components, these components should not be limited by these terms. These components are only used to distinguish one component from another.

Throughout the specification, the term "switching device" refers to a wiring device configured to facilitate a flow of electric current through electric and electronic devices or to block the flow of electric current. The switching device includes transistors that connect the flow of current in accordance with a control signal, and may include a bipolar junction transistor (BJT) and a field effect transistor (FET), without being limited thereto.

However, when the switching device operates as an FET, the switching device includes a gate terminal, a drain terminal, and a source terminal. Here, it is apparent that the drain terminal may function as the source terminal, and the source terminal may also function as the drain terminal in accordance with an input signal.

In addition, switching devices may be classified according to operating voltage into low voltage switching devices (LN) which operate at a relatively low voltage and high voltage switching devices (HN) which operate at a relatively high voltage. In particular, the high voltage switching device HN is a switching device capable of standing against a high voltage applied to a drain terminal and has been widely used in various power devices.

Examples of the high voltage switching device include a double-diffused MOSFET (DMOSFET), an insulated gate bipolar transistor (IGBT), an extended drain MOSFET (ED-MOSFET), and a lateral double-diffused MOSFET (LD-MOSFET), without being limited thereto.

In addition, throughout the specification, the term "turn on" refers to changing a switching device from a non-conductive state into a conductive state, and more particularly, to supplying a signal to a gate such that current flows through the switching device. Conversely, the term "turn off" refers to changing a switching device from a conductive state into a non-conductive state.

Hereinafter, exemplary embodiments will be described in detail with reference to the accompanying drawings. A circuit blocking high voltage will be described. However, the exemplary embodiments are not particularly limited to the circuit blocking high voltage, and may also be applied to general voltage blocking circuits, voltage blocking switches, and the like.

Figure 1:
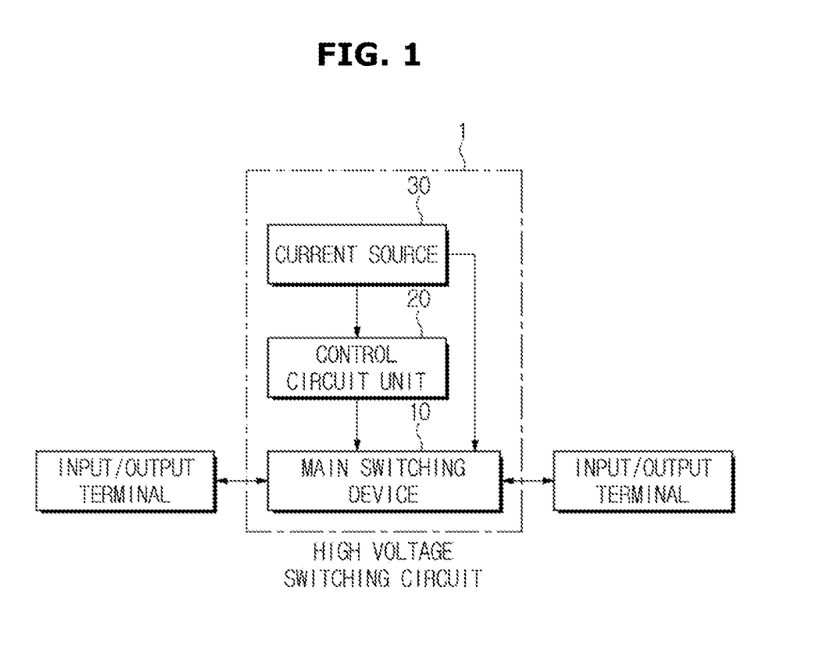
FIG. 1 is a block diagram illustrating a high voltage switching circuit, according to an exemplary embodiment.
Figure 2:
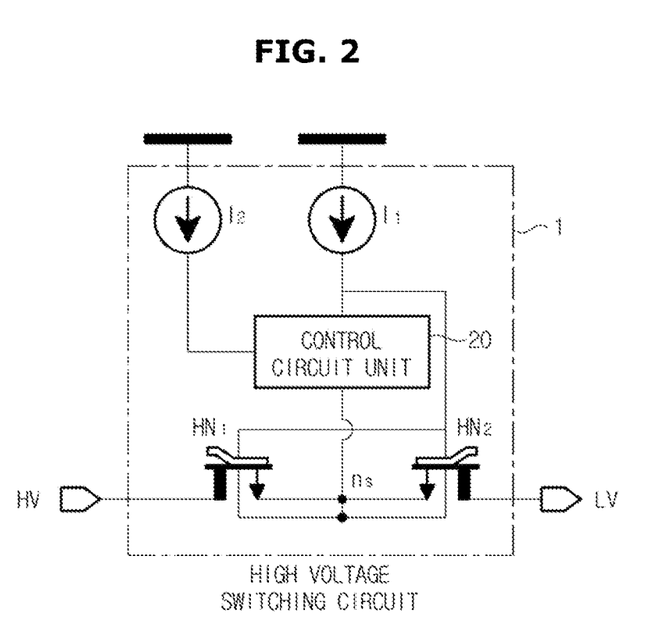
FIG. 2 is a circuit diagram of a high voltage switching circuit, according to an exemplary embodiment.

FIG. 1 is a block diagram illustrating a high voltage switching circuit, according to an exemplary embodiment. FIG. 2 is a circuit diagram of a high voltage switching circuit, according to an exemplary embodiment.

As illustrated in FIGS. 1 and 2, a high voltage switching circuit 1 according to an exemplary embodiment is connected between a first input/output terminal HV and a second input/output terminal LV in series and turned on and off in accordance with a control signal. Hereinafter, the first input/output terminal HV will be described as an input terminal, and the second input/output terminal LV will be described as an output terminal, without being limited thereto. Also, the first input/output terminal and the second input/output terminal may be bi-directional terminals, and the second input/output terminal may be used as an input terminal, and the first input/output terminal also be used as an output terminal.

The high voltage switching circuit 1 includes one or more main switching devices $HN_1$ and $HN_2$ 10 and a control circuit unit (also referred to herein as a "control circuit") 20, and may further include one or more current sources $I_1$ and $I_2$ 30. Here, the current sources $I_1$ and $I_2$ 30 may be external current sources, separate power supply circuits, or power supply devices. Hereinafter, operations of each component will be described in detail.

First, the main switching devices $HN_1$ and $HN_2$ 10 may be connected to the current sources $I_1$ and $I_2$ 30, and may be implemented using high voltage NMOS transistors. Referring to FIGS. 1 and 2, a first main switching device $HN_1$ and a second main switching device $HN_2$ are turned on or off in accordance of a signal of a first current source $I_1$, and the turn-on or turn-off operation is performed when the first current source $I_1$ charges or discharges gate terminals of the first main switching device $HN_1$ and the second main switching device $HN_2$.

In addition, the first main switching device $HN_1$ is connected between the first input/output terminal HV and a terminal $n_s$ in series and supplies current or voltage in response to a turn-on signal of the first current source $I_1$.

Meanwhile, when the first main switching device $HN_1$ is implemented using a high voltage NMOS transistor, a gate terminal may be connected to the first current source $I_1$, a drain terminal may be connected to the first input/output terminal HV, and a source terminal may be connected to a source terminal of the second main switching device $HN_2$.

In addition, the second main switching device $HN_2$ is connected between the second input/output terminal LV and the terminal $n_s$ in series, and supplies current or voltage in response to a turn-on signal of the first current source $I_1$.

Meanwhile, when the second main switching device $HN_2$ is implemented using a high voltage NMOS transistor, a gate terminal may be connected to the first current source $I_1$, a drain terminal may be connected to the second input/output terminal LV, and the source terminal may be connected to the source terminal of the first main switching device $HN_1$.

Then, the control circuit unit turns on or off the first main switching device $HN_1$ and the second main switching device $HN_2$ by controlling a voltage difference between the gate terminal and the source terminal of each of the first main switching device $HN_1$ and the second main switching device $HN_2$ within a predetermined range, for example, in the range of 0 V to 1.8 V.

Particularly, the control circuit unit is turned on and off in response to a signal of the second current source $I_2$ and is connected between the first current source $I_1$ and the terminal ns in series.

For example, when a maximum allowable potential difference between the gate terminal and the source terminal of each of the first and second main switching devices $HN_1$ and $HN_2$ 10 is 1.8 V, the potential difference between the gate terminal and the source terminal should be controlled within the range of 0 V to 1.8 V to turn on or off the first and second main switching devices $HN_1$ and $HN_2$ 10.

In this regard, a source potential of the first and second main switching devices $HN_1$ and $HN_2$ 10 may not be outside of a range of a minimum potential allowable in the circuit, e.g., −25 V, to a maximum operating potential of a low voltage switching device included in the control circuit unit, e.g., 0 V. Thus, the operating potential of the gate terminal should be controlled within the range of −25 V to 1.8 V while the potential difference between the gate terminal and the source terminal is controlled within the range of 0 V to 1.8 V.

In particular, the control circuit unit controls potentials of the gate terminals and the source terminals of the first and second main switching devices $HN_1$ and $HN_2$ 10 such that the potential difference between the gate terminal and the source terminal of each of the first and second main switching devices $HN_1$ and $HN_2$ 10 is maintained within a constant range (e.g., in the range of 0 V to 1.8 V).

Figure 3:
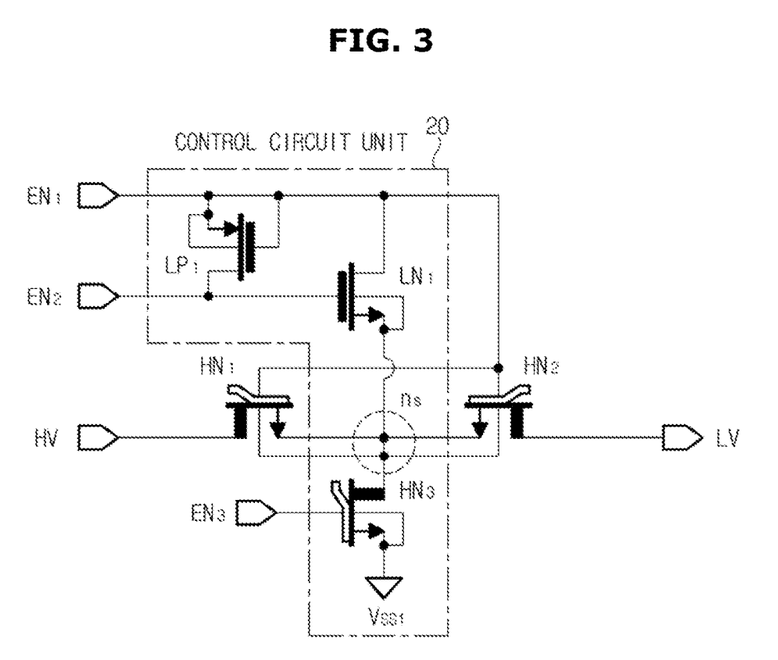
FIG. 3 is a diagram which illustrates a control circuit unit, according to an exemplary embodiment.

FIG. 3 is a diagram which illustrates a control circuit unit, according to an exemplary embodiment. Referring to FIG. 3, the control circuit unit may include two low voltage switching devices $LP_1$ and $LN_1$ and one high voltage switching device $HN_3$.

The low voltage switching device $LP_1$ is turned on or off by a signal of terminals $EN_1$ and $EN_2$ and connected between the terminals $EN_1$ and $EN_2$ in series. The low voltage switching device $LP_1$ may be implemented using a low voltage PMOS transistor. In addition, the terminal $EN_1$ may be connected to the first current source $I_1$, and the terminal $EN_2$ may be connected to the second current source $I_2$.

For example, when the low voltage switching device $LP_1$ is implemented using the low voltage PMOS transistor, a gate terminal may be connected to the terminal $EN_1$, a drain terminal may be connected to the terminal $EN_2$, and a source terminal may be connected to the terminal $EN_1$.

The low voltage switching device $LN_1$ is turned on or off by a signal of the terminals $EN_1$ and $EN_2$ and connected between the terminal $EN_2$ and the terminal ns in series. The low voltage switching device $LN_1$ may be implemented using a low voltage NMOS transistor.

For example, when the low voltage switching device LN1 is implemented using the low voltage NMOS transistor, a gate terminal may be connected to the terminal $EN_2$, a drain terminal may be connected to the terminal $EN_1$, and a source terminal may be connected to the terminal ns.

The high voltage switching device HN3 is turned on or off by a signal of a terminal $EN_3$, which will be described below, and connected between the terminal ns and a first voltage source terminal $V_{ss1}$ in series. The first voltage source terminal $V_{ss1}$ may supply a minimum potential allowable in the circuit, e.g., −25V, and the high voltage switching device $HN_3$ may be implemented using a high voltage NMOS transistor.

For example, when the high voltage switching device $HN_3$ is implemented using the high voltage NMOS transistor, a gate terminal may be connected to the terminal $EN_3$, a drain terminal may be connected to the terminal ns, and a source terminal may be connected to the first voltage source terminal $V_{ss1}$.

Meanwhile, the signal supplied from the terminal $EN_1$ and the signal supplied from the terminal $EN_2$ may respectively include a current supplied from the first current source $I_1$ and a current supplied from the second current source $I_2$. The signal supplied from the terminal $EN_1$ controls turning-on or turning-off of the low voltage switching device $LP_1$ and the first and second main switching devices $HN_1$ and $HN_2$, the signal supplied from the terminal $EN_2$ controls turning-on and/or turning-off of the low voltage switching device $LN_1$, and the signal supplied from the terminal $EN_3$ controls turning-on and/or turning-off of the high voltage switching device $HN_3$. A method for controlling the high voltage switching circuit will be described below with reference to FIGS. 5, 6, and 7.

The high voltage switching circuit as described above may control the potential difference of the terminals of each the first and second main switching devices $HN_1$ and $HN_2$ not to exceed the maximum allowable potential difference by using two low voltage switching devices $LP_1$ and $LN_1$ and one high voltage switching device $HN_3$, and may block a potential of the first input/output terminal HV, which is outside of the operating range of the high voltage switching device, for example, less than −25 V or greater than 25 V, with a small area by using the two low voltage switching devices $LP_1$ and $LN_1$ and one high voltage switching device $HN_3$.

Figure 4:
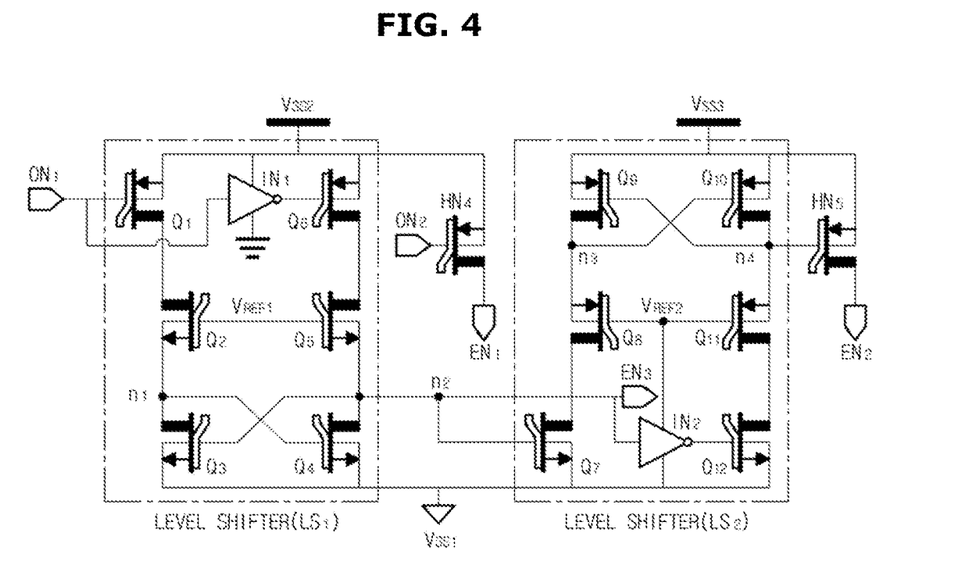
FIG. 4 is a diagram illustrating a control signal generating circuit unit, according to an exemplary embodiment.

Meanwhile, the terminals $EN_1$, $EN_2$, and $EN_3$ may receive signals from a separate control signal generating circuit unit. FIG. 4 is a diagram illustrating a control signal generating circuit unit, according to an exemplary embodiment.

Referring to FIG. 4, the control signal generating circuit unit (also referred to herein as a "control signal generating circuit") may be implemented using one or more level shifters $LS_1$ and $LS_2$ and one or more high voltage switching devices $HN_4$ and $HN_5$. For example, the control signal generating circuit unit may be implemented using two level shifters $LS_1$ and $LS_2$ and two high voltage switching devices $HN_4$ and $HN_5$.

First and second level shifters $LS_1$ and $LS_2$ shift an input potential to another potential and output the shifted potential, and are controlled by shifter control signals $ON_1$ and $ON_2$. In this regard, the shifting includes inverting the potential, in addition to the shifting of the input potential to another potential.

The first level shifter $LS_1$ may shift a first shifter control signal $ON_1$ and may supply the shifted control signal to the terminal $EN_3$. A second shifter control signal $ON_2$ controls turning-on and/or turning-off of the high voltage switching device $HN_4$ by charging and/or discharging the high voltage switching device $HN_4$. The high voltage switching device $HN_4$ and the fifth high voltage switching device $HN_5$ may be implemented using high voltage PMOS transistors.

The first level shifter $LS_1$ may receive power from a second voltage source terminal $V_{ss2}$ and the first voltage source terminal $V_{ss1}$, may be turned on or off by the second shifter control signal $ON_2$ in a state of being connected to the high voltage switching device $HN_4$ in series, and may supply current to the terminal $EN_1$. Here, the terminal $EN_1$ may have a potential equal to or greater than a potential of the first voltage source terminal $V_{ss1}$, e.g., −25 V, and equal to or less than a potential of the second voltage source terminal $V_{ss2}$, e.g., −1.8 V. Meanwhile, the second voltage source terminal $V_{ss2}$ may supply the same potential as the maximum potential difference between the gate terminal and the source terminal of each of the first and second main switching devices $HN_1$ and $HN_2$.

In addition, the first level shifter $LS_1$ may include six high voltage switching devices $Q_1$, $Q_2$, $Q_3$, $Q_4$, $Q_5$, and $Q_6$, and one inverter $IN_1$. Hereinafter, components thereof will be described.

The high voltage switching device $Q_1$ may be implemented using a high voltage PMOS transistor and may be connected between the second voltage source terminal $V_{ss2}$ and the high voltage switching device $Q_2$ in series. In addition, the high voltage switching device $Q_1$ is turned on or off by the first shifter control signal $ON_1$.

For example, when the high voltage switching device $Q_1$ is implemented using the high voltage PMOS transistor, a gate terminal may be connected to an output terminal of the first shifter control signal $ON_1$, a drain terminal may be connected to a drain terminal of the high voltage switching device $Q_2$, and a source terminal may be connected to the second voltage source terminal $V_{ss2}$.

The high voltage switching device $Q_2$ may be implemented using a high voltage NMOS transistor and may be connected between the high voltage switching device $Q_1$ and a terminal $n_1$ in series. In addition, the high voltage switching device $Q_2$ may be turned on or off by a reference signal $V_{REF1}$.

For example, when the high voltage switching device $Q_2$ is implemented using a high voltage NMOS transistor, a gate terminal may be connected to a gate terminal of the high voltage switching device $Q_5$, a drain terminal may be connected to the drain terminal of the high voltage switching device $Q_1$, and the source terminal $n_1$ may be connected to a gate terminal of the high voltage switching device $Q_4$.

The high voltage switching device $Q_3$ may be implemented using a high voltage NMOS transistor and may be connected between the terminal $n_1$ and the first voltage source terminal $V_{ss1}$ in series. In addition, the high voltage switching device $Q_3$ may be turned on or off by a control signal of a terminal $n_2$.

For example, when the high voltage switching device $Q_3$ is implemented using the high voltage NMOS transistor, a gate terminal may be connected to the terminal $n_2$, a drain terminal may be connected to the gate terminal of the high voltage switching device $Q_4$, and a source terminal may be connected to the first voltage source terminal $V_{ss1}$.

The high voltage switching device $Q_4$ may be implemented using a high voltage NMOS transistor and may be connected between the first voltage source terminal $V_{ss1}$ and the terminal $n_2$ in series. In addition, the high voltage switching device $Q_4$ may be turned on or off by a control signal of the terminal $n_1$. The terminal $n_2$ may be the terminal $EN_3$, and the terminal $EN_3$ may turn on and/or off the high voltage switching device $HN_3$ by charging and/or discharging the high voltage switching device $HN_3$ as described above.

For example, when the high voltage switching device $Q_4$ is implemented using the high voltage NMOS transistor, a gate terminal may be connected to the terminal $n_1$, a drain terminal $n_2$ may be connected to the gate terminal of the high voltage switching device $Q_3$, and a source terminal may be connected to the first voltage source terminal $V_{ss1}$.

The high voltage switching device $Q_5$ may be implemented using a high voltage NMOS transistor and may be connected between the terminal $n_2$ and the high voltage switching device $Q_6$. In addition, the high voltage switching device $Q_5$ may be turned on or off by the reference signal $V_{REF1}$.

For example, when the high voltage switching device $Q_5$ is implemented using the high voltage NMOS transistor, a gate terminal may be connected to the gate terminal of the high voltage switching terminal $Q_2$, a drain terminal may be connected to a drain terminal of the high voltage switching device $Q_6$, and a source terminal may be connected to the drain terminal $n_2$ of the high voltage switching device $Q_4$.

The high voltage switching device $Q_6$ may be implemented using a high voltage PMOS transistor and may be connected between the high voltage switching device $Q_5$ and the second voltage source terminal $V_{ss2}$ in series. In addition, the high voltage switching device $Q_6$ may be turned on or off by an output signal of the inverter $IN_1$.

For example, when the high voltage switching device $Q_6$ is implemented using the high voltage PMOS transistor, a gate terminal may be connected to an output terminal of the inverter $IN_1$, the drain terminal may be connected to the drain terminal of the high voltage switching device $Q_5$, and a source terminal may be connected to the second voltage source terminal $V_{ss2}$.

The inverter $IN_1$ outputs a signal to the gate terminal of the high voltage switching device $Q_6$ by using the first shifter control signal $ON_1$ as an input, thereby controlling turning-on and/or turning-off of the high voltage switching device $Q_6$. In addition, the inverter $IN_1$ may receive power from the second voltage source terminal $V_{ss2}$.

Meanwhile, the second level shifter $LS_2$ may receive power from the first voltage source terminal $V_{ss1}$ and a third voltage source terminal $V_{ss3}$, may be turned on or off by a signal from a terminal $n_4$ in a state of being connected to the high voltage switching device $HN_5$ in series, and may supply current to the terminal $EN_2$. Here, the terminal $EN_2$ may have a potential equal to or greater than the potential of the first voltage source terminal $V_{ss1}$, e.g., −25 V, and equal to or less than the potential of the third voltage source terminal $V_{ss3}$, e.g., 0 V. Meanwhile, the third voltage source terminal $V_{ss3}$ may supply the same voltage as a maximum operating potential of the low voltage switching device, e.g., 0 V.

In addition, the second level shifter $LS_2$ may include six high voltage switching devices $Q_7$, $Q_8$, $Q_9$, $Q_{10}$, $Q_{11}$, and $Q_{12}$, and one inverter $IN_2$. Hereinafter, components thereof will be described.

The high voltage switching device $Q_7$ may be implemented using a high voltage NMOS transistor and may be connected between the first voltage source terminal $V_{ss1}$ and the high voltage switching device $Q_8$ in series. In addition, the high voltage switching device $Q_7$ may be turned on or off by a control signal of the terminal $n_2$. Here, the terminal $n_2$ may be a terminal $EN_3$, and the terminal $EN_3$ may turn on and/or off the high voltage switching device $HN_3$ by charging and/or discharging the high voltage switching device $HN_3$.

For example, when the high voltage switching device $Q_7$ is implemented using the high voltage NMOS transistor, a gate terminal may be connected to the drain terminal $n_2$ of the high voltage switching device $Q_4$, a drain terminal may be connected to a drain terminal of the high voltage switching device $Q_8$, and a source terminal may be connected to the first voltage source terminal $V_{ss1}$.

The high voltage switching device $Q_8$ may be implemented using a high voltage PMOS transistor and may be connected between the high voltage switching device $Q_7$ and a terminal $n_3$ in series. In addition, the high voltage switching device $Q_8$ may be turned on and/or off by a reference signal $V_{REF2}$.

For example, when the high voltage switching device $Q_8$ is implemented using the high voltage PMOS transistor, a gate terminal may be connected to a gate terminal of the high voltage switching device $Q_{11}$, a drain terminal may be connected to the drain terminal of the high voltage switching device $Q_7$, and the source terminal may be connected to a drain terminal of the high voltage switching device $Q_9$.

The high voltage switching device $Q_9$ may be implemented using a high voltage PMOS transistor and may be connected between the terminal $n_3$ and the third voltage source terminal $V_{ss3}$ in series. In addition, the voltage switching device $Q_9$ may be turned on and/or off by a control signal of a terminal $n_4$.

For example, when the high voltage switching device $Q_9$ is implemented using the high voltage PMOS transistor, a gate terminal may be connected to a gate terminal $n_4$ of the high voltage switching device $HN_5$, a drain terminal may be connected to the source terminal of the high voltage switching device $Q_8$, and a source terminal may be connected to the third voltage source terminal $V_{ss3}$.

The high voltage switching device $Q_{10}$ may be implemented using a high voltage PMOS transistor and may be connected between the third voltage source terminal $V_{ss3}$ and the terminal $n_4$ in series. In addition, the high voltage switching device $Q_{10}$ may be turned on and/or off by a control signal of the terminal $n_3$.

For example, when the high voltage switching device $Q_{10}$ is implemented using the high voltage PMOS transistor, a gate terminal may be connected to a drain terminal $n_3$ of the high voltage switching device $Q_9$, a drain terminal may be connected to a source terminal of the high voltage switching device $Q_{11}$, and a source terminal may be connected to the third voltage source terminal $V_{ss3}$.

The high voltage switching device $Q_{11}$ may be implemented using a high voltage PMOS transistor and may be connected between the terminal $n_4$ and the high voltage switching device $Q_{12}$ in series. In addition, the high voltage switching device $Q_{11}$ may be turned on and/or off by the reference signal $V_{REF2}$. Here, the reference signal $V_{REF2}$ may be a voltage source (power supply) of the inverter $IN_2$.

For example, when the high voltage switching device $Q_{11}$ is implemented using the high voltage PMOS transistor, a gate terminal may be connected to the gate terminal of the high voltage switching device $Q_8$, a drain terminal may be connected to a drain terminal of the high voltage switching device $Q_{12}$, and a source terminal $n_4$ may be connected to a gate terminal of the high voltage switching device $HN_5$.

The high voltage switching device $Q_{12}$ may be implemented using a high voltage NMOS transistor and may be connected between the high voltage switching device $Q_{11}$ and the first voltage source terminal $V_{ss1}$ in series. In addition, the high voltage switching device $Q_{12}$ may be turned on and/or off by an output signal of the inverter $IN_2$.

For example, when the high voltage switching device $Q_{12}$ is implemented using the high voltage NMOS transistor, the gate terminal may be connected to an output terminal of the inverter $IN_2$, a drain terminal may be connected to the drain terminal of the high voltage switching device $Q_{11}$, and a source terminal $n_4$ may be connected to the first voltage source terminal $V_{ss1}$.

The inverter $IN_2$ may output a signal to the gate terminal of the high voltage switching device $Q_{12}$ by using a signal from the terminal $n_3$ as an input, thereby controlling turning-on and/or turning-off of the high voltage switching device $Q_{12}$. In addition, the inverter $IN_2$ may receive power $V_{REF2}$ from the gate terminals of the high voltage switching devices $Q_8$ and $Q_{11}$.

Figure 5:
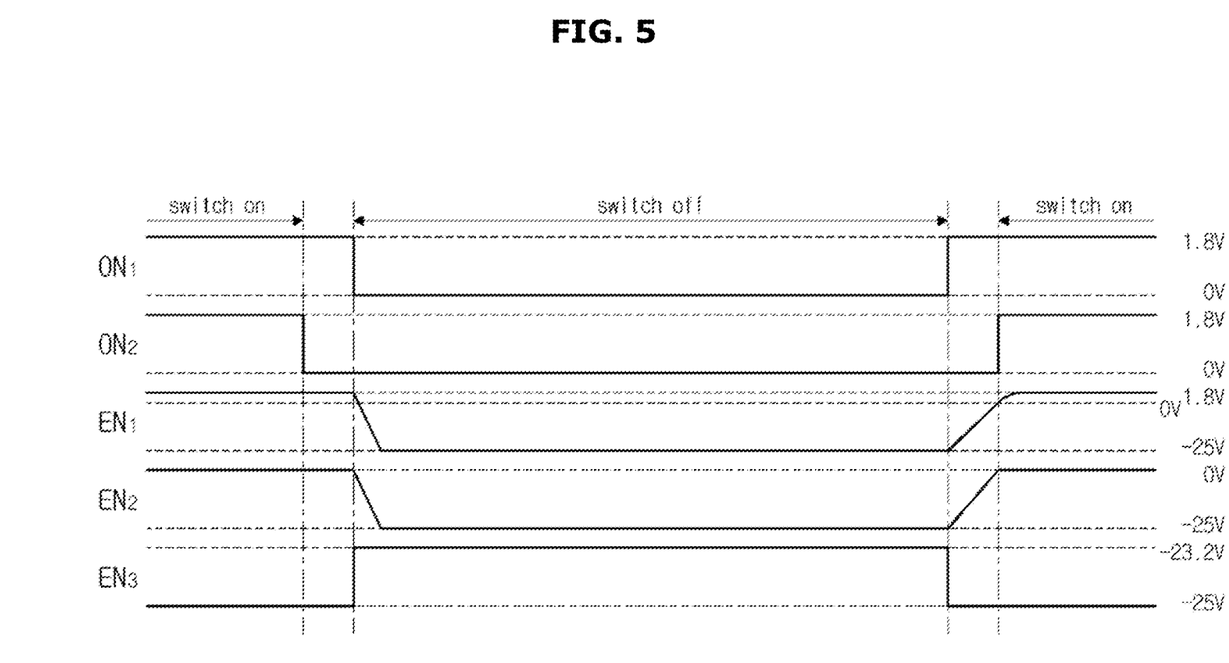
FIG. 5 is a graph illustrating potential changes as a function of time in a high voltage switching circuit, according to an exemplary embodiment.
Figure 6:
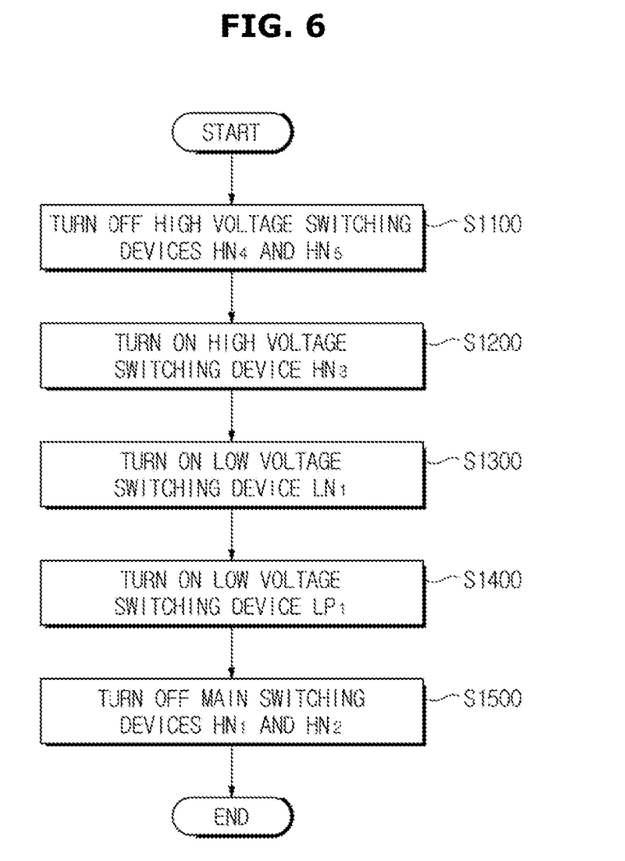
FIG. 6 is a flowchart illustrating a method for controlling a high voltage switching circuit when main switching devices in a turn-on state are turned off.
Figure 7:
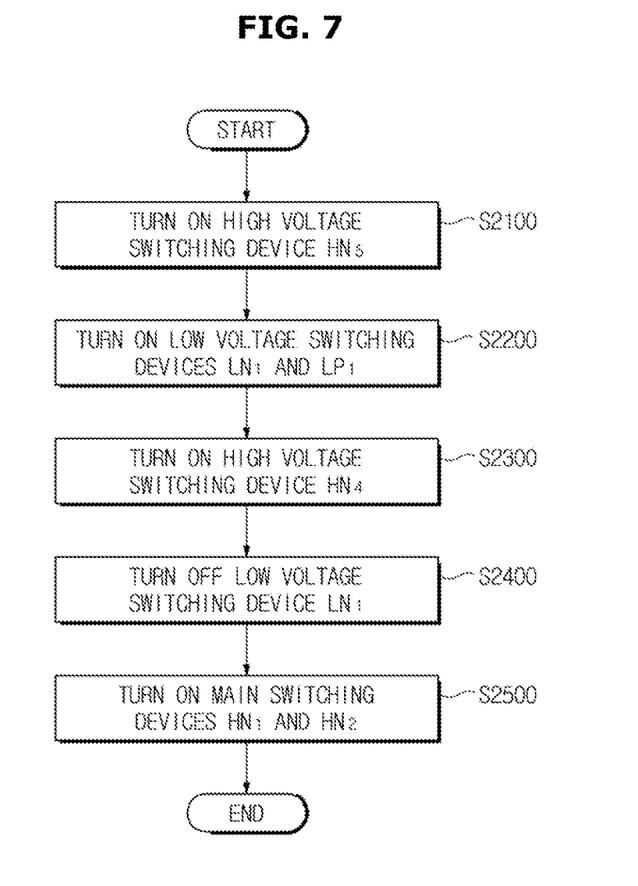

FIG. 5 is a graph illustrating potential changes as a function of time in a high voltage switching circuit, according to an exemplary embodiment. FIG. 6 is a flowchart illustrating a method for controlling a high voltage switching circuit when main switching devices $HN_1$ and $HN_2$ in a turn-on state are turned off. FIG. 7 is a flowchart illustrating a method for controlling a high voltage switching circuit when the main switching devices $HN_1$ and $HN_2$ in a turn-off state are turned on.

Referring to FIGS. 5 and 6, in operation S1100, when the first shifter control signal $ON_1$ and the second shifter control signal $ON_2$ are supplied in order to turn off the main switching devices $HN_1$ and $HN_2$ in a turn-on state, for example, a zero-volt (0 V) signal is supplied to a state of 1.8 V, the high voltage switching devices $HN_4$ and $HN_5$ are turned off, and the terminal EN has a potential, e.g., −23.2 V, shifted from the first shifter control signal $ON_1$, e.g., 0 V, by the first level shifter $LS_1$.

Then, in operation S1200, the high voltage switching device $HN_3$ is turned on by a difference, e.g., 1.8 V, between a potential of the terminal $EN_3$, e.g., −23 V, and a potential of the first voltage source terminal $V_{ss1}$, e.g., −25 V. As the high voltage switching device $HN_3$ is turned on, the terminal $n_s$ is discharged to the potential of the first voltage source terminal $V_{ss1}$, e.g., −25 V, and the low voltage switching device $LN_1$ is turned on due to the discharging of the terminal $n_s$ in operation S1300.

In this regard, as the low voltage switching device $LN_1$ is turned on, the gate terminal $EN_1$ of the low voltage switching device $LP_1$ is discharged to the potential of the first voltage source terminal $V_{ss1}$, e.g., −25 V, and the low voltage switching device $LP_1$ is turned on in operation S1400.

As the low voltage switching device $LP_1$ is turned on, the gate terminal $EP_2$ of the low voltage switching device is discharged to the potential of the first voltage source terminal $V_{ss1}$, e.g., −25 V.

Accordingly, the main switching devices $HN_1$ and $HN_2$ are also discharged to the potential of the first voltage source terminal $V_{ss1}$, e.g., −25 V, and in operation S1500, the main switching devices $HN_1$ and $HN_2$ are turned off.

A potential difference between the gate terminal and the source terminal of the low voltage switching device $LN_1$ and a potential difference between the gate terminal and the source terminal of the low voltage switching device $LP_1$ may be determined in accordance with an amount of current flowing through the high voltage switching device $HN_3$ and width/length (W/L) ratios of the low voltage switching device $LN_1$ and the low voltage switching device $LP_1$.

In particular, by controlling the amount of current flowing through the terminal $n_s$ and the first voltage source and the W/L ratio, the potential difference between the gate terminal and the source terminal of each of the main switching devices $HN_1$ and $HN_2$ may be controlled within a predetermined range. In this aspect, the predetermined range refers to an allowable potential difference with respect to turning on and/or off the main switching devices $HN_1$ and $HN_2$.

Meanwhile, referring to FIGS. 5 and 7, when the high voltage switching device $HN_5$ is turned on in operation S2100 in order to turn on the main switching devices $HN_1$ and $HN_2$ in a turn-off state, the terminal $EN_2$ is charged, thereby turning on the low voltage switching device $LN_1$ and the low voltage switching device $LP_1$ in operation S2200, and the terminal $n_s$ is charged to, for example, zero volts (0 V).

After a predetermined time period, the high voltage switching device $HN_4$ is turned on in operation S2300, and thus the terminal $EN_1$ is charged to a potential of the second voltage source, e.g., 1.8 V, and the terminal $EN_2$ is charged to a potential of the third voltage source, e.g., 0 V.

Accordingly, the low voltage switching device $LN_1$ is turned off in operation S2400, and the main switching devices $HN_1$ and $HN_2$ may be turned on in operation S2500 due to a constant potential difference between the gate terminal and the source terminal thereof, e.g., 1.8 V.

As described above, the high voltage switching circuit according to the illustrated exemplary embodiment may block a voltage greater than an upper limit by controlling the potential difference of the terminals of the main switching device via the control circuit unit, and may have a smaller area than a conventional high voltage switching circuit by controlling the potential difference of the terminals of the main switching device by using switching devices.

In addition, the high voltage switching circuit according to the illustrated exemplary embodiment may turn on or off the main switching devices not by supplying current to a resistor, but by using another switching device. Thus, the high voltage switching circuit may share the current source and/or the control signal with another main switching device.

Meanwhile, a high voltage switching circuit according to another exemplary embodiment may be connected to a transducer of an ultrasonic diagnostic apparatus, and may be used to protect a low voltage-receiving circuit from a signal output from a transmission circuit.

For example, if a voltage supplied from a voltage source is greater than a driving voltage of a transducer, a probe of the ultrasonic diagnostic apparatus may control the transducer by blocking the high voltage.

An ultrasonic imaging apparatus is an apparatus which is configured to acquire a soft tissue tomogram and/or a blood stream image in a non-invasive manner by emitting ultrasonic waves toward a desired region in an object from the surface of the object and receiving ultrasonic signals reflected by the desired region (i.e., ultrasonic echo signals).

Because the ultrasonic imaging apparatus is small and inexpensive, displays an image in real time, and provides a high degree of safety as a result of the lack of X-ray exposure, by comparison with other image diagnostic apparatuses such as an X-ray diagnosis apparatus, a computerized tomography (CT) scanner, a magnetic resonance imaging (MRI) apparatus, and a nuclear medicine diagnostic apparatus. Thus, the ultrasonic imaging apparatus has been widely used for heart diagnosis, celiac diagnosis, urinary diagnosis, and obstetric diagnosis.

The ultrasonic diagnostic apparatus includes a probe configured to emit ultrasonic waves toward an object and to receive ultrasonic echo signals reflected by the object in order to acquire an image of the inside of the object.

A user may acquire an ultrasonic image while rotating the probe in a state of moving along the surface of the object or in contact with the surface of the object.

Figure 8:
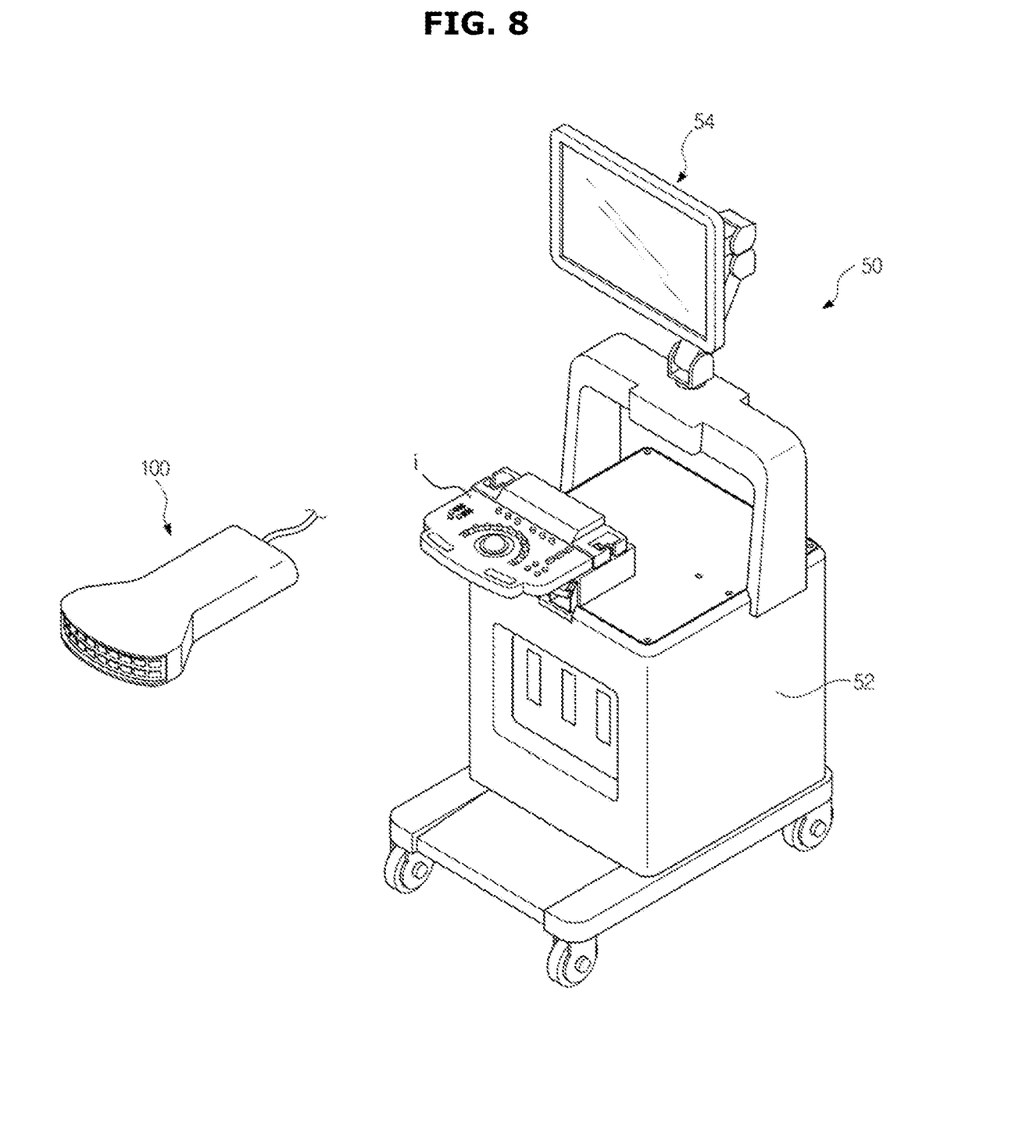
FIG. 8 is a perspective view illustrating an ultrasonic diagnostic apparatus which includes a probe, according to an exemplary embodiment.
Figure 9:
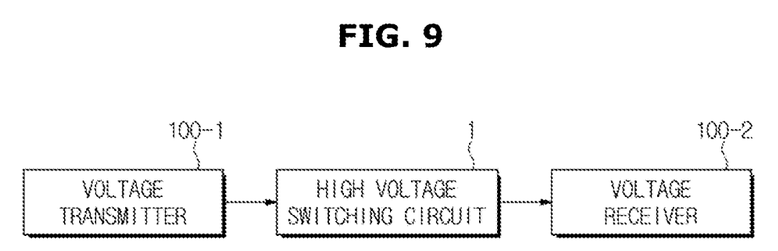
FIG. 9 is a block diagram illustrating the probe of the ultrasonic diagnostic apparatus illustrated in FIG. 8.

FIG. 8 is a perspective view illustrating an ultrasonic diagnostic apparatus which includes a probe, according to an exemplary embodiment. FIG. 9 is a block diagram illustrating the probe of the ultrasonic diagnostic apparatus illustrated in FIG. 8.

First, referring to FIG. 8, an ultrasonic diagnostic apparatus 50 is provided with a probe 100. The ultrasonic diagnostic apparatus 50 includes a main body 52 configured to control and manipulate the ultrasonic diagnostic apparatus 50 and a display unit (also referred to herein as a "display device" and/or as a "display") 54 configured to display an ultrasonic image generated by the main body 52.

The probe 100 according to the illustrated exemplary embodiment transmits ultrasonic signals to an object, receives ultrasonic echo signals reflected by the object, and transmits the received ultrasonic echo signals to the main body 52 in order to acquire an ultrasonic image of the object.

As illustrated in FIG. 9, the probe 100 may include a voltage transmitter 100-1, a high voltage switching circuit 1, and a voltage receiver 100-2. The voltage transmitter 100-1 may be implemented using a power receiver (not shown), and the voltage receiver 100-2 may be implemented using a transducer (not shown).

The power receiver may receive power to drive the transducer from an external device. The power receiver may be implemented by using a 'module' or a 'circuit'. In this regard, the 'module' refers to a software element or a hardware element such as a field programmable gate array (FPGA) or an application specific integrated circuit (ASIC), and the module performs predetermined functions. However, the 'module' is not limited to the software or hardware. The 'module' may be configured to be implemented in a storage medium which is capable of being addressed, and may also be configured to be executed by using one or more processors.

The high voltage switching circuit 1 may include one or more main switching devices $HN_1$ and $HN_2$ 10 and the control circuit unit 20, and may further include one or more current sources $I_1$ and $I_2$ 30, as illustrated in FIGS. 1 and 2.

The high voltage switching circuit 1 may be connected to the power receiver of the probe 100 in a state of being integrated in the probe 100 or via a cable in a state of being externally located with respect to the probe 100.

The high voltage switching circuit 1 may be configured to block a high voltage received from the power receiver of the probe 100 and to transmit, to the transducer, a driving signal for driving the transducer. In this regard, one of the input/output terminals HV and LV of the high voltage switching circuit 1 may be connected to the power receiver, and the other may be connected to the transducer. The high voltage switching circuit 1 is described above in detail with reference to FIGS. 1 to 7, and thus descriptions thereof will not be repeated herein.

The transducer includes a piezoelectric layer configured to perform interconversion between electric signals and acoustic signals while a piezoelectric material vibrates, a matching layer configured to reduce a difference in acoustic impedance between the piezoelectric layer and the object in order to efficiently transfer ultrasonic waves generated by the piezoelectric layer to the object, and a lens layer configured to focus ultrasonic waves which propagate forward from the piezoelectric layer to a predetermined point.

The transducer mounted in the probe 100 may swing, or the driving of the transducer may be inhibited, in accordance with a received voltage. Since the transducer is not driven at a potential greater than a predetermined reference potential, the transducer may be protected from high voltage by the high voltage switching circuit, and may swing by receiving a lower potential.

In the aforementioned exemplary embodiment, some of the components of the high voltage switching circuit and the ultrasound probe may be implemented by using a 'module'. Here, the 'module' refers to a software element or a hardware element such as a field programmable gate array (FPGA) or an application specific integrated circuit (ASIC), and the module performs predetermined functions. However, the module is not limited to the software or hardware. The module may be configured to be implemented in a storage medium which is capable of being addressed, and may also be configured to be executed by one or more processors.

Thus, a module may include, by way of example, any one or more of components, such as software components, object-oriented software components, class components and task components, processes, functions, attributes, procedures, subroutines, segments of program code, drivers, firmware, microcode, circuitry, data, databases, data structures, tables, arrays, and variables. The functionality provided in the components and modules and units may be combined into fewer components and modules, or may further be separated into additional components and modules. Furthermore, the components and modules may be executed by one or more central processing units (CPUs) in a device.

In addition, other exemplary embodiments can also be implemented through computer readable code/instructions in/on a medium, e.g., a transitory or non-transitory computer readable medium, in order to control at least one processing element to implement any above-described exemplary embodiment. The medium can correspond to any transitory or non-transitory medium/media which is configured to permit the storage and/or transmission of the computer readable code.

The computer readable code can be recorded/transferred on a medium in a variety of ways, with examples of the medium including recording media, such as magnetic storage media (e.g., ROM, floppy disks, and hard disks) and optical recording media (e.g., CD-ROMs and DVDs), and transmission media such as Internet transmission media. Thus, the medium may include such a defined and measurable structure including or carrying a signal or information, such as a device carrying a bitstream, according to one or more exemplary embodiments. The medium may also be embodied as a distributed network, so that the computer readable code is stored/transferred and executed in a distributed fashion. Furthermore, the processing element could include a processor or a computer processor, and processing elements may be distributed and/or included in a single device.

As is apparent from the above description, the high voltage switching circuit and the ultrasound probe according to the above-described exemplary embodiments may be configured to block a voltage which is outside of an allowable range of a device by controlling a potential difference of the terminals of the main switching device via the control circuit unit.

In addition, the high voltage switching circuit and the ultrasound probe may share the current source and/or the control signal with another high voltage switching circuit by controlling the potential difference of the terminals of the main switching device via the control circuit unit.

Although a few exemplary embodiments have been shown and described, it will be appreciated by those of skill in the art that changes may be made in these exemplary embodiments without departing from the principles and spirit of the present disclosure, the scope of which is defined in the claims and their equivalents.

What is claimed is:

1. An ultrasound probe comprising:
   a transducer; and
   a voltage switching circuit configured to control a signal received by the transducer by blocking a signal which has a potential that is greater than a reference potential,
   wherein the voltage switching circuit comprises at least one main switching device connected to at least one current source, and a control circuit configured to control a potential difference between respective terminals of each of the at least one main switching device by receiving current from the at least one current source such that the potential difference is within a predetermined range,
   wherein the control circuit comprises a first voltage switching device, a second voltage switching device, and a third voltage switching device,
   wherein the first voltage switching device and the second voltage switching device are configured to operate in a first voltage range, and
   wherein the third voltage switching device is configured to operate in a second voltage range higher than the first voltage range.

2. The ultrasound probe according to claim 1, wherein a first main switching device from among the at least one main switching device is connected to a first current source from among the at least one current source and a first input/output terminal of the voltage switching circuit, and a second main switching device from among the at least one main switching device is connected to the first current source and a second input/output terminal of the voltage switching circuit.

3. The ultrasound probe according to claim 1, wherein the first voltage switching device is controlled by a first current source from among the at least one current source, and the second voltage switching device is controlled by a second current source from among the at least one current source.

4. The ultrasound probe according to claim 1, wherein the first voltage switching device includes a p-type metal-oxide-semiconductor (PMOS) transistor, and
wherein each of the second voltage switching device, the third voltage switching device, a first main switching device from among the at least one main switching device, and a second main switching device from among the at least one main switching device includes an n-type metal-oxide-semiconductor (NMOS) transistor.

5. The ultrasound probe according to claim 1, wherein the potential difference between the respective terminals of the at least one main switching device includes a potential difference between a respective gate terminal and a respective source terminal of the at least one main switching device, and a first current source from among the at least one current source is configured to charge or discharge the respective gate terminal of the at least one main switching device and to control the control circuit, and a second current source from among the at least one current source is configured to control the control circuit.

6. The ultrasound probe according to claim 1, wherein the voltage switching circuit further comprises a control signal generating circuit configured to control the at least one current source.

7. The ultrasound probe according to claim 6, wherein the control signal generating circuit comprises at least one level shifter.

8. The ultrasound probe according to claim 7, wherein each of the at least one level shifter comprises at least one voltage switching device and an inverter.

* * * * *